(12) United States Patent
Fan et al.

(10) Patent No.: US 11,880,974 B2
(45) Date of Patent: Jan. 23, 2024

(54) METHOD AND DEVICE FOR DETECTING CIRCULATING ABNORMAL CELLS

(71) Applicants: ZHUHAI SANMED BIOTECH LTD., Zhuhai (CN); ZHUHAI HENGQIN SANMED AITECH INC., Zhuhai (CN)

(72) Inventors: Xianjun Fan, Zhuhai (CN); Xingjie Lan, Zhuhai (CN); Xin Ye, Zhuhai (CN); Yi Zhang, Zhuhai (CN); Congsheng Li, Zhuhai (CN)

(73) Assignees: ZHUHAI SANMED BIOTECH LTD., Zhuhai (CN); ZHUHAI HENGQIN SANMED AITECH INC., Zhuhai (CN)

( * ) Notice: Subject to any disclaimer, the term of this patent is extended or adjusted under 35 U.S.C. 154(b) by 0 days.

(21) Appl. No.: 18/012,585

(22) PCT Filed: Dec. 4, 2020

(86) PCT No.: PCT/CN2020/133954
§ 371 (c)(1),
(2) Date: Dec. 22, 2022

(87) PCT Pub. No.: WO2021/258651
PCT Pub. Date: Dec. 30, 2021

(65) Prior Publication Data
US 2023/0306588 A1    Sep. 28, 2023

(30) Foreign Application Priority Data

Jun. 23, 2020   (CN) .......................... 202010585145.8

(51) Int. Cl.
*G06T 7/00* (2017.01)
*G06V 20/70* (2022.01)
(Continued)

(52) U.S. Cl.
CPC ............ *G06T 7/0012* (2013.01); *G06T 5/002* (2013.01); *G06T 5/20* (2013.01); *G06T 7/11* (2017.01);
(Continued)

(58) Field of Classification Search
CPC ......... G06T 7/0012; G06T 7/11; G06T 5/002; G06T 5/20; G06T 2207/10056;
(Continued)

(56) References Cited

U.S. PATENT DOCUMENTS

| 2010/0317002 A1 | 12/2010 | Daniely et al. |
| 2019/0156481 A1 | 5/2019 | Sekiguchi et al. |
| 2023/0041229 A1* | 2/2023 | Tahvilian ................ G06T 7/136 |

FOREIGN PATENT DOCUMENTS

| CN | 102270307 A | 12/2011 |
| CN | 102682305 A | 9/2012 |

(Continued)

OTHER PUBLICATIONS

Li et al. "Ellipsoidal mirror dark-field scanning for detection of circulating tumor cells" (Year: 2019).*
(Continued)

*Primary Examiner* — Vu Le
*Assistant Examiner* — Winta Gebreslassie
(74) *Attorney, Agent, or Firm* — Womble Bond Dickinson (US) LLP

(57) ABSTRACT

A method and device for detecting circulating abnormal cells. The method for detecting the circulating abnormal cells comprises: respectively segmenting and labelling, by using an image processing algorithm and a morphological algorithm, cell nuclei included in dark field microscope images of a plurality of probe channels (101); inputting the dark field microscope images, in which cell nuclei are labelled, of the plurality of probe channels into a pre-built
(Continued)

circulating abnormal cell detection model to acquire the number of staining signals included in each labelled cell nucleus in the dark field microscope image of each probe channel (102); and for each labelled cell nucleus, on the basis of the number of the staining signals included in the labelled cell nucleus in the acquired dark field microscope image of each probe channel, determining whether the labelled cell nucleus belongs to a circulating abnormal cell (103). The method can effectively improve the reliability of detecting the circulating abnormal cells.

11 Claims, 3 Drawing Sheets

(51) Int. Cl.
*G06T 7/11* (2017.01)
*G06V 20/69* (2022.01)
*G06V 10/774* (2022.01)
*G06T 5/20* (2006.01)
*G06T 5/00* (2006.01)

(52) U.S. Cl.
CPC .......... *G06V 10/774* (2022.01); *G06V 20/695* (2022.01); *G06V 20/698* (2022.01); *G06V 20/70* (2022.01); *G06T 2207/10056* (2013.01); *G06T 2207/20036* (2013.01); *G06T 2207/20081* (2013.01); *G06T 2207/30024* (2013.01); *G06T 2207/30096* (2013.01); *G06V 2201/03* (2022.01)

(58) Field of Classification Search
CPC . G06T 2207/20036; G06T 2207/20081; G06T 2207/30024; G06T 2207/30096; G06V 20/695; G06V 20/07; G06V 20/698; G06V 10/774; G06V 2201/03

USPC .......................................................... 382/133
See application file for complete search history.

(56) References Cited

FOREIGN PATENT DOCUMENTS

| | | |
|---|---|---|
| CN | 106296635 A | 1/2017 |
| CN | 109523520 A | 3/2019 |
| CN | 109991205 A | 7/2019 |
| CN | 110501278 A | 11/2019 |
| CN | 111126162 A | 5/2020 |
| CN | 111175267 A | 5/2020 |
| CN | 111739010 A | 10/2020 |
| JP | 2019513228 A | 5/2019 |

OTHER PUBLICATIONS

Jiang, Zhongmin et al., "Circulating Tumor Cells, Circulating Genetically Abnormal Cells and Early Diagnosis of Lung Cancer", Journal of Precision Medicine; vol. 35, No. 2, Apr. 30, 2020.
Office Action dated Aug. 31, 2023 for Japanese Patent Application No. 2022-580447.
Extended European Search Report dated Nov. 27, 2023 for European Patent Application No. 20941819.3.
Katz et al.; "Genetically Abnormal Circulating Cells in Lung Cancer Patients: An Antigen-Independent Flourescence in Situ Hybridization-Based Case-Control Study", Clinical Cancer Researchm vol. 16; No. 15; Aug. 1, 2010, pp. 3976-3987.
Mocan et al.; "Automatic Detection of Tumor Cells in Microscopic Images of Unstained Blood using Convolutional Neural Networks", 2018 IEEE 14th International Conference on Intelligent Computer Communication and Processing (ICCP) Sep. 6, 2018; pp. 319-324.

* cited by examiner ial Stage of International
METHOD AND DEVICE FOR DETECTING CIRCULATING ABNORMAL CELLS

CROSS-REFERENCE TO RELATED APPLICATIONS

This Application is a National Stage of International Application No. PCT/CN2020/133954, filed on Dec. 4, 2020, which claims the benefit of a priority of Chinese Patent Application No. 202010585145.8 and titled "METHOD AND DEVICE FOR DETECTING CIRCULATING ABNORMAL CELLS", filed with the China National Intellectual Property Administration on Jun. 23, 2020, the entire contents of all of which are incorporated herein by reference.

TECHNICAL FIELD

The present disclosure relates to the technical field of cell detection, in particular to a method and a device for detecting circulating abnormal cells (CACs).

BACKGROUND

Circulating tumor cells (CTCs) are cells that are shed from primary tumors and form secondary tumors in distant organ sites during tumor metastasis. A large number of studies have shown that the number of CTCs in blood can predict the disease progression and indicate the response of the tumor to chemotherapy drugs. Therefore, by collecting a certain amount of peripheral blood, detecting CTCs in the peripheral blood and monitoring changes of CTCs' content in the blood, it is possible to analyze the pathogenesis of tumors and evaluate the prognosis of patients, and thus understand the improvement of patients' clinical status and drug resistance after receiving treatment.

In recent years, circulating genetically abnormal cells (CACs) have been reported to be found in the peripheral blood of patients with non-small cell lung cancer (NSCLC). These cells are of a type considered to be involved in the occurrence, progression, and metastasis of lung cancer, including CTCs that are shed from the tumor and enter the peripheral blood circulation system. The detection of CACs in peripheral blood makes it possible to predict the existence of tumor earlier. This method undoubtedly has a broad prospect for application.

At present, the method of detecting CACs is to collect the dark field (DF) microscope images of peripheral blood, label CACs in the DF microscope images based on the morphological information of CACs such as shape and/or size and based on manual intervention, count the labelled CACs, and determine the content of CACs in blood based on the counting results. However, this method for detecting CACs is based on the morphological information of CACs in combination with manual intervention to detect, determine, and count CACs, so the detection is rather subjective and not reliable. Also, the detection efficiency is low and the detection cost is high due to the need for manual participation.

SUMMARY

In view of the foregoing, an object of the present disclosure is to provide a method and a device for detecting circulating abnormal cells to improve the reliability of detection of circulating abnormal cells.

In a first aspect, an embodiment of the present disclosure provides a method for detecting circulating abnormal cells, comprising:

segmenting and labelling cell nuclei included in dark field microscope images of a plurality of probe channels respectively, by using an image processing algorithm and a morphological algorithm;

inputting the dark field microscope images, in which the cell nuclei are labelled, of the plurality of probe channels into a pre-built circulating abnormal cell detection model to acquire the number of staining signals included in each of the labelled cell nuclei in the dark field microscope image of each of the probe channels; and for each of the labelled cell nuclei; determining whether the labelled cell nucleus belongs to a circulating abnormal cell, based on the acquired number of the staining signals included in the labelled cell nucleus in the dark field microscope image of each of the probe channels.

With reference to the first aspect, an embodiment of the present disclosure provides a first possible implementation of the first aspect, wherein building the circulating abnormal cell detection model comprises:

segmenting and labelling cell nuclei included in dark field microscope sample images of a plurality of probe channels respectively by using the image processing algorithm and the morphological algorithm, and segmenting the dark field microscope sample images, in which the cell nuclei are labelled, of the probe channels to acquire a plurality of cell nucleus sample images;

for each of the cell nucleus sample images, performing a convolution process several times on the cell nucleus sample image to acquire a first feature image, a second feature image, a third feature image and a fourth feature image, respectively;

performing a convolution process on the fourth feature image to acquire a fifth feature image, and performing upsampling on the fifth feature image to acquire a sixth feature image;

performing a convolution process on the third feature image and the sixth feature image to acquire a seventh feature image, and performing upsampling on the seventh feature image to acquire an eighth feature image;

performing a convolution process on the second feature image and the eighth feature image to acquire a ninth feature image, and performing upsampling on the ninth feature image to acquire a tenth feature image;

performing a convolution process on the first feature image and the tenth feature image to acquire an eleventh feature image; and training and testing a deep learning network by taking each of the cell nucleus sample images as an input of the deep learning network, fusing the seventh, ninth, and eleventh feature images as output prediction results in three scales of the deep learning network, and finally taking the number of staining signals included in the labelled cell nuclei in the cell nucleus sample images as the output of the deep learning network, to acquire a circulating abnormal cell detection model.

With reference to the first possible implementation of the first aspect, an embodiment of the present disclosure provides a second possible implementation of the first aspect, wherein performing a convolution process several times on a cell nucleus sample image to respectively acquire a first feature image, a second feature image, a third feature image and a fourth feature image comprises:

sequentially performing a convolution process of a first convolution layer, a second convolution layer, a third convolution layer and a fourth convolution layer on the cell nucleus sample image to acquire a first feature image;

performing a convolution process of a fifth convolution layer and a sixth convolution layer on the first feature image to acquire a second feature image;

performing a convolution process of a seventh convolution layer and an eighth convolution layer on the second feature image to acquire a third feature image; and.

performing a convolution process of a ninth convolution layer and a tenth convolution layer on the third feature image to acquire a fourth feature image.

With reference to the second possible implementation of the first aspect, an embodiment of the present disclosure provides a third possible implementation of the first aspect, wherein sequentially performing a convolution process of a first convolution layer, a second convolution layer, a third convolution layer and a fourth convolution layer on the cell nucleus sample image to acquire a first feature image comprises that:

a size of the cell nucleus sample image is 320*320, the number of convolution kernels of the first convolution layer is 32, a size of the convolution kernel is 3*3 and a step size is 1, and a size of the output feature image is 320*320;

the second convolution layer comprises a first convolution sublayer and a second convolution sublayer, wherein the number of convolution kernels of the first convolution sublayer is 32, a size of the convolution kernel is 3*3 and a step size is 2, and a size of the output feature image is 160*160; and the number of convolution kernels of the second convolution sublayer is 64, a size of the convolution kernel is 1*1 and a step size is 1, and a size of the output feature image is 160*160;

the third convolution layer comprises a third convolution sublayer and a fourth convolution sublayer, wherein the number of convolution kernels of the third convolution sublayer is 64, a size of the convolution kernel is 3*3 and a step size is 1, and a size of the output feature image is 160*160; and the number of convolution kernels of the fourth convolution sublayer is 128, a size of the convolution kernel is 1*1 and a step size is 2, and a size of the output feature image is 80*80; and the fourth convolution layer comprises a fifth convolution sublayer and a sixth convolution sublayer, wherein the number of convolution kernels of the fifth convolution sublayer is 128, a size of the convolution kernel is 3*3 and a step size is 1, and a size of the output feature image is 80*80; and the number of convolution kernels of the sixth convolution sublayer is 128, a size of the convolution kernel is 1*1 and a step size is 1, and a size of the output feature image is 80*80, wherein the feature image output by the sixth convolution sublayer is the first feature image.

With reference to the first aspect and any one of the first possible implementation to the third possible implementation of the first aspect, an embodiment of the present disclosure provides a fourth possible implementation of the first aspect, wherein segmenting and labelling cell nuclei included in dark field microscope images of a plurality of probe channels respectively by using the image processing algorithm and the morphological algorithm comprises:

for a dark field microscope image of each of the probe channels, performing Gaussian kernel filtering on the dark field microscope image to acquire a denoised image;

labelling connected domains of the denoised image to acquire labelled connected domains; and segmenting the acquired connected domains by using the morphological algorithm, and labelling the segmented domains to acquire the labelled cell nuclei.

With reference to the first aspect and any one of the first possible implementation to the third possible implementation of the first aspect, an embodiment of the present disclosure provides a fifth possible implementation of the first aspect, wherein inputting the dark field microscope images, in which the cell nuclei are labelled, of the plurality of probe channels into a pre-built circulating abnormal cell detection model to acquire the number of staining signals included in each of the labelled cell nuclei in the dark field microscope image of each of the probe channels comprises:

inputting a dark field microscope image, in which the cell nuclei are labelled, of a first probe channel into the circulating abnormal cell detection model to acquire a first count of staining signals included in each of the labelled cell nuclei in the dark field microscope image, in which the cell nuclei are labelled, of the first probe channel;

inputting a dark field microscope image, in which the cell nuclei are labelled, of a second probe channel into the circulating abnormal cell detection model to acquire a second count of staining signals included in each of the labelled cell nuclei in the dark field microscope image, in which the cell nuclei are labelled, of the second probe channel;

inputting a dark field microscope image, in which the cell nuclei are labelled, of a third probe channel into the circulating abnormal cell detection model to acquire a third count of staining signals included in each of the labelled cell nuclei in the dark field microscope image, in which the cell nuclei are labelled, of the third probe channel; and inputting a dark field microscope image, in which the cell nuclei are labelled, of a fourth probe channel into the circulating abnormal cell detection model to acquire a fourth count of staining signals included in of the labelled cell nuclei in the dark field microscope image, in which the cell nuclei are labelled, of the fourth probe channel.

With reference to the fifth possible implementation of the first aspect, an embodiment of the present disclosure provides a sixth possible implementation of the first aspect, wherein for each of the labelled cell nuclei, determining whether the labelled cell nucleus belongs to a circulating abnormal cell, based on the acquired number of the staining signals included in the labelled cell nucleus in the dark field microscope image of each of the probe channels comprises:

acquiring a first count of staining signals included in a first labelled cell nucleus in a dark field microscope image, in which the cell nuclei are labelled, of a first probe channel;

acquiring a second count of staining signals included in the first labelled cell nucleus in a dark field microscope image, in which the cell nuclei are labelled, of a second probe channel;

acquiring a third count of staining signals included in the first labelled cell nucleus in a dark field microscope image, in which the cell nuclei are labelled, of a third probe channel;

acquiring a fourth count of staining signals included in the first labelled cell nucleus in a dark field microscope image, in which the cell nuclei are labelled, of a fourth probe channel; and determining whether the first labelled cell nucleus belongs to a circulating abnormal cell based on the first count, the second count, the third count and the fourth count of the staining signals.

In a second aspect, an embodiment of the present disclosure further provides a device for detecting circulating abnormal cells, comprising:

a cell nucleus labelling module configured to segment and label nuclei included in dark field microscope images of a plurality of probe channels respectively by using the image processing algorithm and the morphological algorithm;

a staining signal number acquisition module configured to input the dark field microscope images, in which the cell nuclei are labelled, of the plurality of probe channels into a pre-built circulating abnormal cell detection model to acquire the number of staining signals included in each of the labelled cell nuclei in the dark field microscope image of each probe channel; and a cell type determination module configured to, for each of the labelled cell nuclei, determine whether the labelled cell nucleus belongs to a circulating abnormal cell based on the acquired number of the staining signals included in the labelled cell nucleus in the dark field microscope image of each probe channel.

In a third aspect, an embodiment of the present disclosure provides a computer device, which comprises a memory, a processor, and a computer program stored in the memory and executable by the processor. When the processor executes the computer program, the steps of the above method are implemented.

In a fourth aspect, an embodiment of the present disclosure provides a computer readable storage medium, on which a computer program is stored, and the computer program, when executed by a processor, performs the steps of the above method.

According to the method and the device for detecting circulating abnormal cells provided by the embodiments of the present disclosure, the cell nuclei included in the dark field microscope images of the plurality of probe channels are respectively segmented and labelled by using the image processing algorithm and the morphological algorithm; the dark field microscope images, in which the cell nuclei are labelled, of the plurality of probe channels are input into the pre-built circulating abnormal cell detection model to acquire the number of the staining signals included in each labelled cell nucleus in the dark field microscope image of each probe channel; and for each of the labelled cell nuclei, it is determined whether the labelled cell nucleus belongs to a circulating abnormal cell, based on the acquired number of the staining signals included in the labelled cell nucleus in the dark field microscope image of each probe channel. In this manner, by using the image processing algorithm and the morphological algorithm to label the cell nuclei, it is possible to label small-sized cell nuclei and avoid the influence of subjectivity. By using the circulating abnormal cell detection model to detect the staining signals included in the labelled cell nuclei, high reliability and accuracy of the detection of the staining signals can be achieved, which in turn can effectively improve the reliability and accuracy of CTCs detection.

In order to make the above object, features and advantages of the present disclosure more obvious and understandable, the following preferred embodiments will be described in detail with reference to the attached drawings.

BRIEF DESCRIPTION OF THE DRAWINGS

In order to more clearly explain the technical solutions of the embodiments of the present disclosure, the drawings that are needed in the embodiments will be briefly introduced below. It is understood that the drawings introduced below only show some embodiments of the present disclosure, so they should not be regarded as limiting the scope. For those of ordinary skill in the art, other relevant drawings can be obtained based on these drawings without spending any creative efforts.

DETAILED DESCRIPTION

Figure 1:
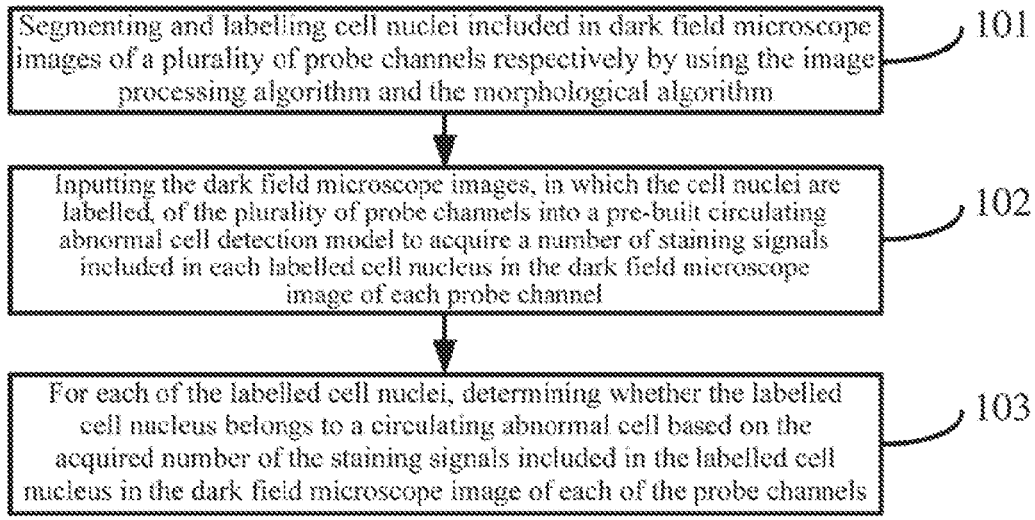
FIG. 1 shows a schematic flow diagram of a method for detecting circulating abnormal cells provided by an embodiment of the present disclosure.

In order to further clarify the purposes, technical solutions and advantages of the embodiments of the present disclosure, the technical solutions in the embodiments of the present disclosure will be clearly and completely described below with reference to the drawings involved in the embodiments of the present disclosure. Obviously, the described embodiments are only part of the embodiments of the present disclosure, but not all of them. Generally, the components in the embodiments of the present disclosure described and shown in the drawings herein can be arranged and designed in various different configurations. Therefore, the following detailed description of the embodiments of the present disclosure shown in the drawings is not intended to limit the scope of the claimed present disclosure, but only represents selected embodiments of the present disclosure. Based on the embodiments of the present disclosure, all other embodiments obtained by those skilled in the art without spending creative efforts are within the scope of protection of the present disclosure.

According to the existing method of detecting the CACs, after collecting dark field microscope images of peripheral blood cells, morphological information of the CACs is used with manual intervention to identify the CACs, and the identified CACs in blood are counted to determine the content of the CACs in blood based on the counting results, which will serve as a reference for subsequent diagnosis and treatment. Since the CACs are identified and counted based on the morphological information of the CACs as well as by the manual intervention, the reliability of detecting (identifying) the CACs is not high and the detection efficiency is low. According to an embodiment of the present disclosure, in a dark field microscope image obtained by fluorescence in situ hybridization (FISH) technology, cell nuclei are automatically segmented, staining (fluorescence) signals in the cell nuclei are counted by using a preset CACs detection model, and CACs are detected and identified based on quantitative determination rules and the counting.

An embodiment of the present disclosure provides a method and a device for detecting circulating abnormal cells, which are described below by way of embodiments.

FIG. 1 shows a schematic flow diagram of a method for detecting circulating abnormal cells provided by an embodiment of the present disclosure. As shown in FIG. 1, the method comprises:

Step 101: Segmenting and labelling cell nuclei included in dark field microscope images of a plurality of probe channels respectively by using the image processing algorithm and the morphological algorithm.

In an embodiment of the present disclosure, the dark field microscope image is an image of cells obtained by staining the cells with DAPI or other cell nucleus dye based on fluorescence in situ hybridization (FISH) technology. DAPI is 4',6-diamidino-2-phenylindole, which is a fluorescent dye that can strongly bind to deoxyribonucleic acid (DNA) and can penetrate through the intact cell membrane for cell staining.

In an alternative embodiment of the present application, the dark field microscope image can be an image containing various types of cells, such as normal cells, circulating abnormal cells and/or single amplified cells, with a resolution of 2448*2048 pixels. One dark field microscope image can contain hundreds of different types of cells.

In an embodiment of the present disclosure, image shooting of a plurality of probe channels is performed. As an alternative embodiment, the probe channels include a first probe channel, a second probe channel, a third probe channel and a fourth probe channel. Correspondingly, the dark field microscope images of the plurality of probe channels include a dark field microscope image of the first probe channel, a dark field microscope image of the second probe channel, a dark field microscope image of the third probe channel and a dark field microscope image of the fourth probe channel, and the staining images of the respective probe channels of each cell nucleus are segmented from the dark field microscope images of the four probe channels.

In an alternative embodiment of the present disclosure, segmenting and labelling the staining signals included in the dark field microscope images of the plurality of probe channels respectively by using the image processing algorithm and the morphological algorithm comprises:

A11: For the dark field microscope image of each probe channel, performing Gaussian kernel filtering on the dark field microscope image to acquire a denoised image.

In an embodiment of the present disclosure, by performing Gaussian kernel filtering on the dark field microscope image, the noise in the dark field microscope image can be removed and a denoised image is obtained. As an alternative embodiment, Gaussian kernel filtering includes, but is not limited to, Gaussian kernel function, self-adaptive Gaussian filter, gamma transform and top-hat transform.

In an alternative embodiment of the present disclosure, before or after performing Gaussian kernel filtering on the dark field microscope image, taking before performing Gaussian kernel filtering on the dark field microscope image as an example, the method may further comprise:

segmenting the dark field microscope image.

In an embodiment of the present disclosure, the dark field microscope image is segmented into 128*128 pieces of subimages, and the resolution of each subimage is 19*16.

A12: Labelling the connected domains of the denoised image to acquire labelled connected domains.

In an embodiment of the present disclosure, the connected domains of the denoised image are labelled by using a connected domain generator algorithm.

A13: By using the morphological algorithm, segmenting the acquired connected domains, and labelling the acquired segmented domains to acquire the labelled cell nuclei.

In an embodiment of the present disclosure, the morphological algorithm includes, but is not limited to, Hough circle detection algorithm, closed operation and/or open operation. For example, for overlapping cells or adherent cells in the segmented connected domains, the core of each cell of the overlapping cells or adherent cells is calculated by Hough circle detection algorithm, such that the overlapping cells or adherent cells are segmented into a plurality of individual cells. For another example, closed operation is performed on the connected domain and then open operation is performed on the connected domain. In this manner, through the morphological algorithm, adjacent cell nuclei can be separated to acquire and label the individual cell nuclei, such that each cell nucleus included in the dark field microscope image can be labelled, avoiding missing any cell nuclei caused by labelling based on the morphological information of CACs.

In an embodiment of the present disclosure, as mentioned above, taking the case where the dark field microscope images of the plurality of probe channels comprise the dark field microscope images of four probe channels as an example, one cell corresponds to the cell nuclei in the dark field microscope images of the four probe channels, respectively, and the dark field microscope images of the four probe channels are interrelated with one another.

In an alternative embodiment of the present disclosure, after acquiring the denoised image and before labelling the connected domains of the denoised image, the method further comprises:

segmenting the denoised image based on binary segmentation algorithm to acquire a binary image, and the connected domains are labelled based on the binary image.

In an embodiment of the present disclosure, the binary segmentation algorithm includes, but is not limited to: Otsu self-adaptive threshold segmentation algorithm, which acquires a binary image containing a foreground color and a background color by performing binary segmentation on the denoised image.

Step 102: Inputting the dark field microscope images, in which the cell nuclei are labelled, of the plurality of probe channels into a pre-built circulating abnormal cell detection model to acquire the number of staining signals included in each labelled cell nucleus in the dark field microscope image of each probe channel.

In an embodiment of the present disclosure, a calibration tool is used to manually calibrate the types of cells in the dark field microscope images in which the cell nuclei are labelled of the plurality of probe channels; and taking the images with calibrated cell types as a training set, a supervised training is performed based on deep learning YOLO-v3-MobileNet algorithm, and then the trained model is used for a staining (fluorescence) signal detection test on a test library, and a final circulating abnormal cell detection model is acquired.

In an embodiment of the present disclosure, if the dark field microscope images of the plurality of probe channels comprise a dark field microscope image of the first probe channel, a dark field microscope image of the second probe channel, a dark field microscope image of the third probe channel and a dark field microscope image of the fourth probe channel, as an alternative embodiment, inputting the dark field microscope images, in which the cell nuclei are labelled, of the plurality of probe channels into a pre-built circulating abnormal cell detection model to acquire the number of staining signals included in each of the labelled cell nuclei in the dark field microscope image of each of the probe channels comprises:

inputting the dark field microscope image, in which the cell nuclei are labelled, of the first probe channel into the circulating abnormal cell detection model to acquire a first count of staining signals included in each of the labelled cell nuclei in the dark field microscope image, in which the cell nuclei are labelled, of the first probe channel;

inputting the dark field microscope image, in which the cell nuclei are labelled, of the second probe channel into the circulating abnormal cell detection model to acquire a second count of staining signals included in each of the labelled cell nuclei in the dark field microscope image; in which the cell nuclei are labelled, of the second probe channel;

inputting the dark field microscope image, in which the cell nuclei are labelled, of the third probe channel into the circulating abnormal cell detection model to acquire a third count of staining signals included in each of the labelled cell nuclei in the dark field microscope image, in which the cell nuclei are labelled, of the third probe channel; and inputting the dark field microscope image, in which the cell nuclei are labelled, of the fourth probe channel into the circulating abnormal cell detection model to acquire a fourth count of staining signals included in each of the labelled cell nuclei in the dark field microscope image, in which the cell nuclei are labelled, of the fourth probe channel.

In an embodiment of the present disclosure, the circulating abnormal cell detection model detects the staining signals included in each of the cell nuclei in the dark field microscope images of the four probe channels, and counts the number of the staining signals.

Step 103: For each of the labelled cell nuclei, determining whether the labelled cell nucleus belongs to a circulating abnormal cell, based on the acquired number of the staining signals included in the labelled cell nucleus in the dark field microscope image of each of the probe channels.

In an alternative embodiment, for each of the labelled cell nuclei, determining whether the labelled cell nucleus belongs to a circulating abnormal cell, based on the acquired number of the staining signals included in the labelled cell nucleus in the dark field microscope image of each of the probe channels comprises:

acquiring a first count of the staining signals included in a first labelled cell nucleus in the dark field microscope image, in which the cell nuclei are labelled, of the first probe channel;

acquiring a second count of the staining signals included in the first labelled cell nucleus in the dark field microscope image, in which the cell nuclei are labelled, of the second probe channel;

acquiring a third count of the staining signals included in the first labelled cell nucleus in the dark field microscope image, in which the cell nuclei are labelled, of the third probe channel;

acquiring a fourth count of the staining signals included in the first labelled cell nucleus in the dark field microscope image, in which the cell nuclei are labelled, of the fourth probe channel; and determining whether the first labelled cell nucleus belongs to a circulating abnormal cell based on the first count, the second count, the third count and the fourth count of the staining signals.

In an alternative embodiment, determining whether the first labelled cell nucleus belongs to a circulating abnormal cell based on the first count, the second count, the third count and the fourth count of the staining signals comprises:

if the number of the counts no less than 2 is greater than 2 among the first count, the second count, the third count and the fourth count of the staining signals, determining that the first labelled cell nucleus belongs to a circulating abnormal cell.

In a further alternative embodiment, the method further comprises:

if any one of the first count, the second count, the third count and the fourth count of the staining signals is less than 2, determining that the first labelled cell nucleus belongs to a deletion cell; if only one of the counts is greater than 2, determining that the first labelled cell nucleus belongs to a single amplified cell; and if the staining signals appear in pairs, determining that the first labelled cell nucleus belongs to a normal cell.

In an embodiment of the present disclosure, for a cell that cannot be identified as a circulating abnormal cell, a deletion cell, a single amplified cell or a normal cell, it is identified as a cell of another type or an unknown cell.

According to the method for detecting circulating abnormal cells provided by the embodiment of the present disclosure, the cell nuclei included in the dark field microscope images of the plurality of probe channels are respectively segmented and labelled by using the image processing algorithm and the morphological algorithm; the dark field microscope images, in which the cell nuclei are labelled, of the plurality of probe channels are input into the pre-built circulating abnormal cell detection model to acquire the number of the staining signals included in each labelled cell nucleus in the dark field microscope image of each probe channel; and for each of the labelled cell nuclei, it is determined whether the labelled cell nucleus belongs to a circulating abnormal cell, based on the acquired number of the staining signals included in the labelled cell nucleus in the dark field microscope image of each probe channel. In this manner, by using the image processing algorithm and the morphological algorithm to label the cell nuclei, it is possible to label small-sized cell nuclei and avoid the influence of subjectivity. By using the circulating abnormal cell detection model to detect the staining signals included in the labelled cell nuclei, high reliability and accuracy of the detection of the staining signals can be achieved, which in turn can effectively improve the reliability and accuracy of CTCs identification based on quantitative determination rules and counting.

Figure 2:
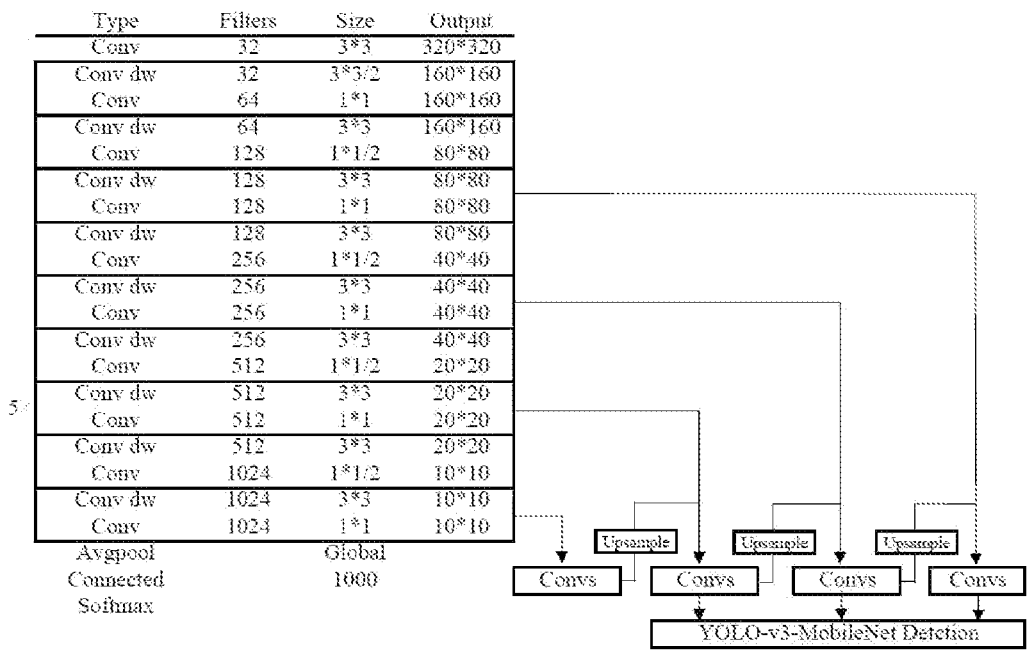
FIG. 2 shows a schematic diagram of a convolution process for building a circulating abnormal cell detection model according to an embodiment of the present disclosure.

FIG. 2 shows a schematic diagram of a convolution process for building a circulating abnormal cell detection model according to an embodiment of the present disclosure.

Figure 3:
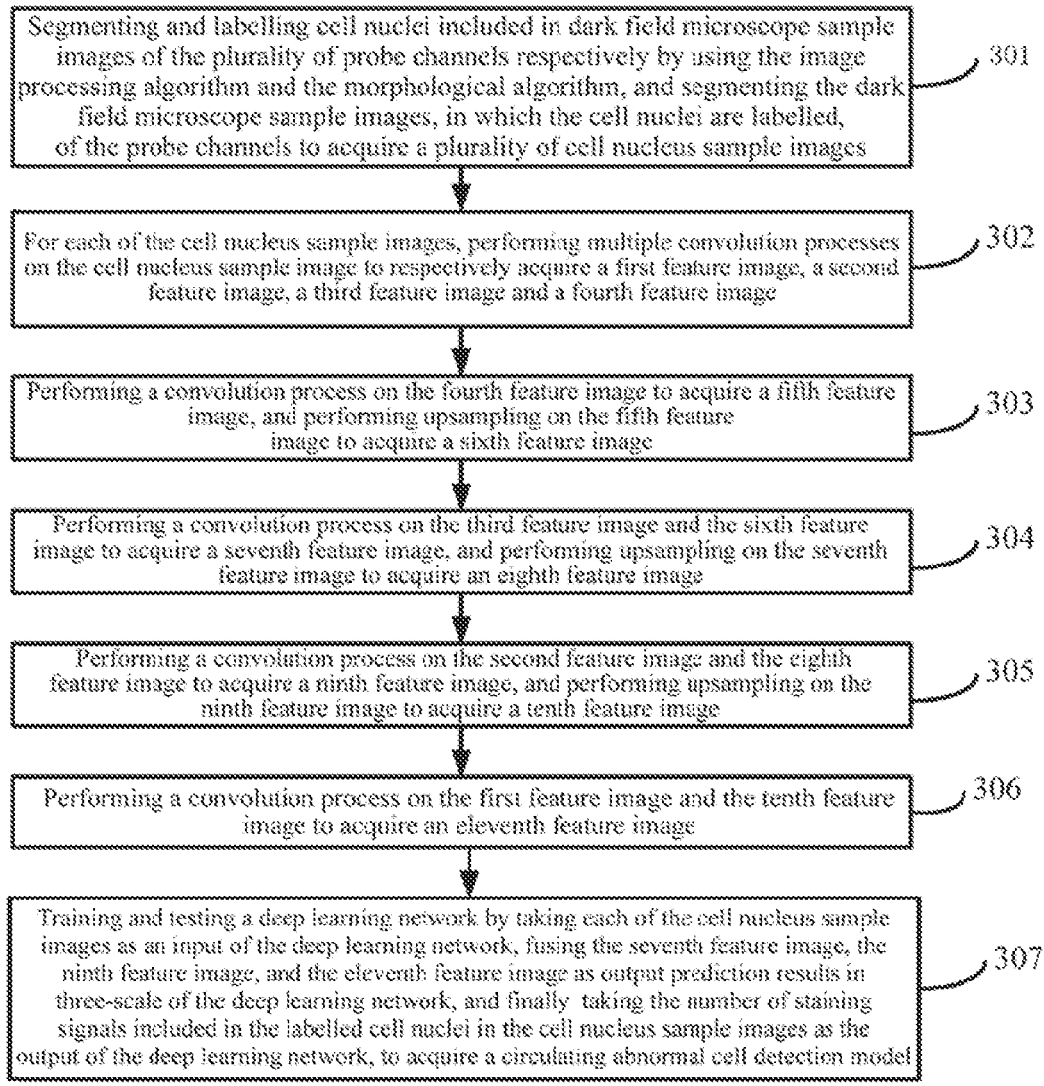
FIG. 3 shows a schematic flow diagram of a method for building a circulating abnormal cell detection model according to an embodiment of the present disclosure.

FIG. 3 shows a schematic flow diagram of a method for building a circulating abnormal cell detection model according to an embodiment of the present disclosure.

As shown in FIG. 2 and FIG. 3, the method comprises:

Step 301: Segmenting and labelling cell nuclei included in dark field microscope sample images of the plurality of probe channels respectively by using the image processing algorithm and the morphological algorithm, and segmenting the dark field microscope sample images, in which the cell nuclei are labelled, of the probe channels to acquire a plurality of cell nucleus sample images.

In an embodiment of the present disclosure, a dark field microscope sample image, in which cell nuclei are labelled, of a probe channel is segmented to acquire a plurality of cell nucleus sample images. In an alternative embodiment of the present disclosure, the size of the cell nucleus sample image is 320*320.

In an embodiment of the present disclosure, the segmented cell nucleus sample image includes normal cells, single amplified cells, deletion cells, circulating abnormal cells and other cells.

Step 302: For each of the cell nucleus sample images, performing a convolution process several times on the cell nucleus sample image to acquire a first feature image, a second feature image, a third feature image and a fourth feature image, respectively.

In an alternative embodiment of the present disclosure, for each cell nucleus sample image of the size of 320*320, the cell nucleus sample image is convolved through a convolution layer to extract characteristics included in the cell nucleus sample image, and the convolved image is output as an input of a next convolution layer.

In an alternative embodiment of the present disclosure, if the size of the cell nucleus sample image is 320*320, feature images of four sizes of 80*80, 40*40, 20*20 and 10*10 are respectively output, that is, the size of the first feature image is 80*80, the size of the second feature image is 40*40, the size of the third feature image is 20*20, and the size of the fourth feature image is 10*10. In this way, the output feature images can not only take into account the high-level semantic features, but also contain detailed characteristics of the staining signals that can be used for identification.

In an alternative embodiment of the present disclosure, performing a convolution process several times on the cell nucleus sample image to respectively acquire a first feature image, a second feature image, a third feature image and a fourth feature image comprises:

A21: Sequentially performing a convolution process of a first convolution layer, a second convolution layer, a third convolution layer and a fourth convolution layer on the cell nucleus sample image to acquire a first feature image.

In an alternative embodiment of the present disclosure, sequentially performing a convolution process of the first convolution layer, the second convolution layer, the third convolution layer and the fourth convolution layer on the cell nucleus sample image to acquire the first feature image comprises that:

a size of the cell nucleus sample image is 320*320, the number of convolution kernels of the first convolution layer is 32, a size of the convolution kernel is 3*3 and a step size is 1, and a size of the output feature image is 320*320;

the second convolution layer comprises a first convolution sublayer and a second convolution sublayer, wherein the first convolution sublayer adopts depthwise separable convolution (Convdw), the number of convolution kernels of the first convolution sublayer is 32, a size of the convolution kernel is 3*3 and a step size is 2, and a size of the output feature image is 160*160; and the number of convolution kernels of the second convolution sublayer is 64, a size of the convolution kernel is 1*1 and a step size is 1, and a size of the output feature image is 160*160;

the third convolution layer comprises a third convolution sublayer and a fourth convolution sublayer, wherein the third convolution sublayer adopts depthwise separable convolution, the number of convolution kernels of the third convolution sublayer is 64, a size of the convolution kernel is 3*3 and a step size is 1, and a size of the output feature image is 160*160 and the number of convolution kernels of the fourth convolution sublayer is 128, a size of the convolution kernel is 1*1 and a step size is 2, and a size of the output feature image is 80*80; and the fourth convolution layer comprises a fifth convolution sublayer and a sixth convolution sublayer, wherein the fifth convolution sublayer adopts depthwise separable convolution, the number of convolution kernels of the fifth convolution sublayer is 128, a size of the convolution kernel is 3*3 and a step size is 1, and a size of the output feature image is 80*80; and the number of convolution kernels of the sixth convolution sublayer is 128, a size of the convolution kernel is 1*1 and a step size is 1, and a size of the output feature image is 80*80, wherein the feature image output by the sixth convolution sublayer is the first feature image.

In an embodiment of the present disclosure, after being processed by a convolution layer with a step size of 1, the size of the image output by this convolution layer is the same as the size of the input image; and after being processed by a convolution layer with a step size of 2, the size of the image output by this convolution layer is half the size of the input image.

A22: Performing the convolution process of the fifth convolution layer and the sixth convolution layer on the first feature image to acquire a second feature image.

In an embodiment of the present disclosure, the fifth convolution layer comprises a seventh convolution sublayer and an eighth convolution sublayer, wherein the seventh convolution sublayer adopts spatial convolution, the number of convolution kernels of the seventh convolution sublayer is 128, a size of the convolution kernel is 3*3 and a step size is 1, and a size of the output feature image is 80*80; and the number of convolution kernels of the eighth convolution sublayer is 256, a size of the convolution kernel is 1*1 and a step size is 2, and a size of the output feature image is 40*40; and the sixth convolution layer comprises a ninth convolution sublayer and a tenth convolution sublayer, wherein the ninth convolution sublayer adopts spatial convolution, the number of convolution kernels of the ninth convolution sublayer is 256, a size of the convolution kernel is 3*3 and a step size is 1, and a size of the output feature image is 40*40; and the number of convolution kernels of the tenth convolution sublayer is 256, a size of the convolution kernel is 1*1 and a step size is 1 and a size of the output feature image is 40*40, wherein the feature image output by the tenth convolution sublayer is the second feature image.

A23: Performing the convolution process of the seventh convolution layer and the eighth convolution layer on the second feature image to acquire a third feature image.

In an embodiment of the present disclosure, the seventh convolution layer comprises an eleventh convolution sublayer and a twelfth convolution sublayer, wherein the eleventh convolution sublayer adopts depthwise separable convolution, the number of convolution kernels of the eleventh convolution sublayer is 256, a size of the convolution kernel is 3*3 and a step size is 1, and a size of the output feature image is 40*40; and the number of convolution kernels of the twelfth convolution sublayer is 512, a size of the convolution kernel is 1*1 and a step size is 2; and a size of the output feature image is 20*20; and the eighth convolution layer comprises a thirteenth convolution sublayer and a fourteenth convolution sublayer, wherein the thirteenth convolution sublayer adopts depthwise separable convolution, the number of convolution kernels of the thirteenth convolution sublayer is 512, a size of the convolution kernel is 3*3 and a step size is 1, and a size of the output feature image is 20*20; and the number of convolution kernels of the fourteenth convolution sublayer is 512, a size of the convolution kernel is 1*1 and a step size is 1, and a size of the output feature image is 20*20, wherein the feature image output by the fourteenth convolution sublayer is the third feature image.

A24: Performing the convolution process of the ninth convolution layer and the tenth convolution layer on the third feature image to acquire a fourth feature image.

In an embodiment of the present disclosure, the ninth convolution layer comprises a fifteenth convolution sublayer and a sixteenth convolution sublayer, wherein the fifteenth convolution sublayer adopts depthwise separable convolution, the number of convolution kernels of the fifteenth convolution sublayer is 512, a size of the convolution kernel is 3*3 and a step size is 1, and a size of the output feature image is 20*20; and the number of convolution kernels of the sixteenth convolution sublayer is 1024, a size of the convolution kernel is 1*1 and a step size is 2, and a size of the output feature image is 10*10; and the tenth convolution layer comprises a seventeenth convolution sublayer and an eighteenth convolution sublayer, wherein the seventeenth convolution sublayer adopts depth wise separable convolution, the number of convolution kernels of the seventeenth convolution sublayer is 1024, a size of the convolution kernel is 3*3 and a step size is 1, and a size of the output feature image is 10*10; and the number of convolution kernels of the eighteenth convolution sublayer is 1024, a size of the convolution kernel is 1*1 and a step size is 1, and a size of the output feature image is 10*10, wherein the feature image output by the eighteenth convolution sublayer is the fourth feature image.

Step 303: Performing a convolution process on the fourth feature image to acquire a fifth feature image, and performing upsampling on the fifth feature image to acquire a sixth feature image.

Step 304: Performing a convolution process on the third feature image and the sixth feature image to acquire a seventh feature image; and performing upsampling on the seventh feature image to acquire an eighth feature image.

Step 305: Performing a convolution process on the second feature image and the eighth feature image to acquire a ninth feature image, and performing upsampling on the ninth feature image to acquire a tenth feature image.

Step 306: Performing a convolution process on the first feature image and the tenth feature image to acquire an eleventh feature image.

Step 307: Training and testing a deep learning network by taking each of the cell nucleus sample images as an input of the deep learning network, fusing the seventh, ninth, and eleventh feature images as output prediction results in three scales of the deep learning network, and finally taking the number of staining signals included in the labelled cell nuclei in the cell nucleus sample images as the output of the deep learning network, to acquire a circulating abnormal cell detection model.

In an alternative embodiment of the present application, the cell nucleus sample images are randomly divided into a training set and a testing set. As an alternative embodiment, the training set accounts for 90% of the total number of the cell nucleus sample images, and the testing set accounts for 10% of the total number of the cell nucleus sample images.

In an alternative embodiment of the present application, for the training set, a 5-fold cross-validation method is used to respectively train the deep learning networks which employ multiple machine learning algorithms, from which the deep learning network with the highest training accuracy is selected as the final circulating abnormal cell detection model.

In an embodiment of the present disclosure, for each cell nucleus labelled in the cell nucleus sample image, the corresponding cell type is pre-calibrated, e.g., whether the cell nucleus belongs to a normal cell, a circulating abnormal cell, a single amplified cell, or a deletion cell, and the number of the staining signals included in the cell nucleus sample images corresponding to the four probe channels for each cell type is also pre-calibrated. For example, for a first labelled cell nucleus in the cell nucleus sample image of the first probe channel, which is calibrated as a deletion cell, the number of the staining signals contained therein is 1; correspondingly, for the first labelled cell nucleus in the cell nucleus sample image of the second probe channel, the number of the staining signals contained therein is 2; for the first labelled cell nucleus in the cell nucleus sample image of the third probe channel, the number of the staining signals contained therein is 1; and for the first labelled cell nucleus in the cell nucleus sample image of the fourth probe channel, the number of the staining signals contained therein is 3. Thus, taking the first cell nucleus as an example, the image of the first cell nucleus in the cell nucleus sample image of the first probe channel is used as an input of the deep learning network, and that the number of the staining signals contained in the first cell nucleus is 1 is used as an output of the deep learning network; the image of the first cell nucleus in the cell nucleus sample image of the second probe channel is used as an input of the deep learning network, and that the number of the staining signals contained in the first cell nucleus is 2 is used as an output of the deep learning network; the image of the first cell nucleus in the cell nucleus sample image of the third probe channel is used as an input of the deep learning network, and that the number of the staining signals contained in the first cell nucleus is 1 is used as an output of the deep learning network; and the image of the first cell nucleus in the cell nucleus sample image of the fourth probe channel is used as an input of the deep learning network, and that the number of the staining signals contained in the first cell nucleus is 3 is used as an output of the deep learning network. In this manner, the deep learning network is trained.

In an alternative embodiment, Labelme and other calibration tools can be used to manually and accurately calibrate 100,000+ cell nucleus images of multiple probe channels, so as to ensure that the boundary morphology of each cell nucleus and each staining signal point is clear and accurate and acquire the cell nucleus sample images. After that, the calibrated cell nucleus sample images are used as a training set and a testing set for supervised training.

In an embodiment of the present disclosure, the deep learning network identifies the input cell nucleus image based on preset rules, and uses a multi-scale feature image, which fuses the seventh feature image, the ninth feature image and the eleventh feature image, for cell nucleus identification. The number of staining signals corresponding to the identified cell nucleus is taken as an output of the deep learning network, and the deep learning network is trained, and finally the circulating abnormal cell detection model is acquired. The input of the circulating abnormal cell detection model is the cell nucleus sample images, and the output is the number of the staining signals included in each of the cell nuclei in the cell nucleus sample images.

In an embodiment of the present disclosure, an output feature image of 10*10 (the fourth feature image) and an output feature image of 20*20 (the third feature image) are subjected to upsampling respectively to double the sizes thereof, and then are respectively fused with a feature image of 20*20 output by the eighth convolution layer and a feature image of 40*40 output by the sixth convolution layer, thereby further increase the diversity of the output feature images.

In an embodiment of the present disclosure, due to the relatively small size of the staining signal image in the dark field microscope image, the existing detection algorithm based on morphology has the disadvantage that small-target staining signal images are easy to miss detection. Therefore, based on the characteristics of the staining signal images, the embodiment of the present application optimizes the detection by adding a feature image of 80*80, which can enrich the texture and contour information, such that the small-target staining signal images can be detected.

In an embodiment of the present disclosure, the deep learning algorithm is an improved deep learning YOLO-v3-Mobilenet algorithm based on the deep learning YOLO-v3 algorithm. Compared with the three-scale scale characteristics (feature images) output by the deep learning YOLO-v3 algorithm framework, the improved deep learning YOLO-v3-Mobilenet algorithm adds a large-scale scale characteristic, cuts off a minimum-scale characteristic output and adds a large-scale characteristic output, such that the three output scale characteristics remain unchanged. In addition, the minimum-scale characteristic is fused with other scale characteristics through upsampling, and the final detection result is the fusion of three output scale characteristics, which takes into account both high-level semantic features and low-level detailed features.

The circulating abnormal cell detection model according to the embodiment of the present disclosure has been tested on the testing set of 10,000+, and the correct detection rate is 95.3%, which shows a significant improvement as compared with the correct detection rate of 90.6% of the deep learning YOLO-v3 algorithm, and the circulating abnormal cell detection model has high sensitivity and specificity.

Figure 4:
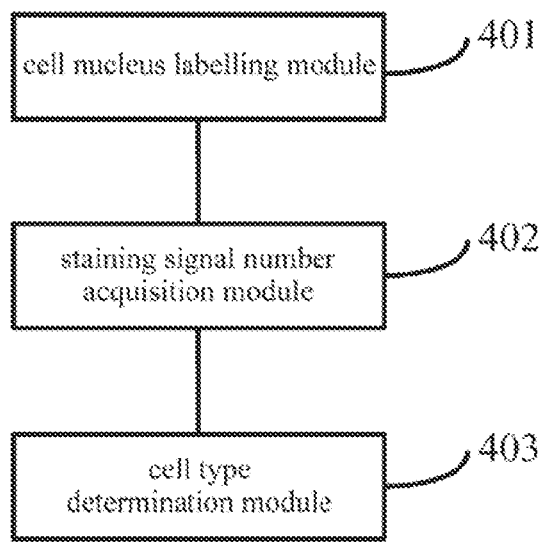
FIG. 4 shows a schematic structural diagram of a device for detecting circulating abnormal cells provided by an embodiment of the present disclosure.

FIG. 4 shows a schematic structural diagram of a device for detecting circulating abnormal cells provided by an embodiment of the present disclosure. As shown in FIG. 4, the device comprises:

a cell nucleus labelling module 401 configured to segment and label cell nuclei included in dark field microscope images of a plurality of probe channels respectively by using the image processing algorithm and the morphological algorithm.

In an embodiment of the present disclosure, the dark field microscope image is an image of cells obtained by staining the cells with DAPI based on the FISH technology. The probe channels include a first probe channel, a second probe channel, a third probe channel and a fourth probe channel. Correspondingly, the dark field microscope images of the plurality of probe channels include a dark field microscope image of the first probe channel, a dark field microscope image of the second probe channel, a dark field microscope image of the third probe channel and a dark field microscope image of the fourth probe channel, and the image of each cell nucleus is segmented respectively from the dark field microscope images of the four probe channels.

In an alternative embodiment of the present disclosure, the cell nucleus labelling module 401 comprises:

a filtering unit (not shown in the drawings) configured to, for the dark field microscope image of each of the probe channels, perform Gaussian kernel filtering on the dark field microscope image to acquire a denoised image;

a connected domain labelling unit configured to label connected domains of the denoised image to acquire labelled connected domains; and a cell nucleus labelling unit configured to segment the acquired connected domains by using the morphological algorithm, and label the acquired segmented domains to acquire labelled cell nuclei.

The device further comprises a staining signal number acquisition module 402 configured to input dark field microscope images, in which the cell nuclei are labelled, of a plurality of probe channels into a pre-built circulating abnormal cell detection model to acquire the number of staining signals included in each of the labelled cell nuclei in the dark field microscope image of each probe channel.

In an alternative embodiment of the present disclosure, the staining signal number acquisition module 402 comprises:

a first count acquisition unit (not shown in the drawings) configured to input the dark field microscope image, in which the cell nuclei are labelled, of the first probe channel into the circulating abnormal cell detection model to acquire a first count of staining signals included in each of the labelled cell nuclei in the dark field microscope image, in which the cell nuclei are labelled, of the first probe channel;

a second count acquisition unit configured to input the dark field microscope image, in which the cell nuclei are labelled, of the second probe channel into the circulating abnormal cell detection model to acquire a second count of staining signals included in each of the labelled cell nuclei in the dark field microscope image, in which the cell nuclei are labelled, of the second probe channel;

a third count acquisition unit configured to input the dark field microscope image, in which the cell nuclei are labelled, of the third probe channel into the circulating abnormal cell detection model to acquire a third count of staining signals included in each of the labelled cell nuclei in the dark field microscope image, in which the cell nuclei are labelled, of the third probe channel; and a fourth count acquisition unit configured to input the dark field microscope image, in which the cell nuclei are labelled, of the fourth probe channel into the circulating abnormal cell detection model to acquire a fourth count of staining signals included in each of the labelled cell nuclei in the dark field microscope image, in which the cell nuclei are labelled, of the fourth probe channel.

The device further comprises a cell type determination module 403 configured to determine, for each of the labelled cell nuclei, whether the labelled cell nuclei belongs to a circulating abnormal cell based on the acquired number of the staining signals included in the labelled cell nucleus in the dark field microscope image of each probe channel.

In an alternative embodiment of the present disclosure, the cell type determination module 403 comprises:

a counting unit of the first probe channel (not shown in the drawings) configured to acquire a first count of the staining signals included in the first labelled cell nucleus in the dark field microscope image, in which the cell nuclei are labelled, of the first probe channel;

a counting unit of the second probe channel configured to acquire a second count of the staining signals included in the first labelled cell nucleus in the dark field microscope image, in which the cell nuclei are labelled, of the second probe channel;

a counting unit of the third probe channel configured to acquire a third count of the staining signals included in the first labelled cell nucleus in the dark field microscope image, in which the cell nuclei are labelled, of the third probe channel;

a counting unit of the fourth probe channel configured to acquire a fourth count of the staining signals included in the first labelled cell nucleus in the dark field microscope image, in which the cell nuclei are labelled, of the fourth probe channel; and a determination unit configured to determine whether the first labelled cell nucleus belongs to a circulating abnormal cell based on the first count, the second count, the third count and the fourth count of the staining signals.

In an alternative embodiment, the determination unit is specifically configured to:

if the number of the counts no less than 2 is greater than 2 among the first count, the second count, the third count and the fourth count of the staining signals, determine that the first labelled cell nucleus belongs to a circulating abnormal cell.

In an alternative embodiment, the determination unit is further specifically configured to:

if any one of the first count, the second count, the third count and the fourth count of the staining signals is less than 2, determine that the first labelled cell nucleus belongs to a deletion cell; if only one of the counts is greater than 2, determine that the first labelled cell nucleus belongs to a single amplified cell; and if the staining signals appear in pairs, determine that the first labelled cell nucleus belongs to a normal cell.

In an alternative embodiment, the device further comprises:

a detection model building module (not shown in the drawings) configured to segment and label the cell nuclei included in the dark field microscope sample images of the plurality of probe channels respectively by using the image processing algorithm and the morphological algorithm, and segment the dark field microscope sample images, in which the cell nuclei are labelled, of the probe channels to acquire a plurality of cell nucleus sample images;

for each of the cell nucleus sample images, perform a convolution process several times on the cell nucleus sample image to acquire a first feature image, a second feature image, a third feature image and a fourth feature image, respectively;

perform a convolution process on the fourth feature image to acquire a fifth feature image, and perform upsampling on the fifth feature image to acquire a sixth feature image;

perform a convolution process on the third feature image and the sixth feature image to acquire a seventh feature image; and perform upsampling on the seventh feature image to acquire an eighth feature image;

perform a convolution process on the second feature image and the eighth feature image to acquire a ninth feature image, and perform upsampling on the ninth feature image to acquire a tenth feature image;

perform a convolution process on the first feature image and the tenth feature image to acquire an eleventh feature image; and train and test a deep learning network by taking each of the cell nucleus sample images as an input of the deep learning network, fuse the seventh, ninth, and eleventh feature images as output prediction results in three scales of the deep learning network, and finally taking the number of staining signals included in the labelled cell nuclei in the cell nucleus sample images as the output of the deep learning network, to acquire a circulating abnormal cell detection model.

In an alternative embodiment of the present disclosure, performing a convolution process several times on the cell nucleus sample image to respectively acquire a first feature image, a second feature image, a third feature image and a fourth feature image comprises:

sequentially performing a convolution process of a first convolution layer, a second convolution layer, a third convolution layer and a fourth convolution layer on the cell nucleus sample image to acquire a first feature image;

performing a convolution process of a fifth convolution layer and a sixth convolution layer on the first feature image to acquire a second feature image;

performing a convolution process of a seventh convolution layer and an eighth convolution layer on the second feature image to acquire a third feature image; and performing a convolution process of a ninth convolution layer and a tenth convolution layer on the third feature image to acquire a fourth feature image.

In an alternative embodiment of the present disclosure, sequentially performing a convolution process of the first convolution layer, the second convolution layer, the third convolution layer and the fourth convolution layer on the cell nucleus sample image to acquire the first feature image comprises that:

a size of the cell nucleus sample image is 320*320, the number of convolution kernels of the first convolution layer is 32, a size of the convolution kernel is 3*3 and a step size is 1, and a size of the output feature image is 320*320;

the second convolution layer comprises a first convolution sublayer and a second convolution sublayer, wherein the first convolution sublayer adopts depthwise separable convolution, the number of convolution kernels of the first convolution sublayer is 32, a size of the convolution kernel is 3*3 and a step size is 2, and a size of the output feature image is 160*160; and the number of convolution kernels of the second convolution sublayer is 64, a size of the convolution kernel is 1*1 and a step size is 1, and a size of the output feature image is 160*160;

the third convolution layer comprises a third convolution sublayer and a fourth convolution sublayer, wherein the third convolution sublayer adopts depthwise separable convolution, the number of convolution kernels of the third convolution sublayer is 64, a size of the convolution kernel is 3*3 and a step size is 1, and a size of the output feature image is 160*160; and the number of convolution kernels of the fourth convolution sublayer is 128, a size of the convolution kernel is 1*1 and a step size is 2, and a size of the output feature image is 80*80; and the fourth convolution layer comprises a fifth convolution sublayer and a sixth convolution sublayer, wherein the fifth convolution sublayer adopts depthwise separable convolution, the number of convolution kernels of the fifth convolution sublayer is 128, a size of the convolution kernel is 3*3 and a step size is 1, and a size of the output feature image is 80*80; and the number of convolution kernels of the sixth convolution sublayer is 128, a size of the convolution kernel is 1*1 and a step size is 1, and a size of the output feature image is 80*80, wherein the feature image output by the sixth convolution sublayer is the first feature image.

Figure 5:
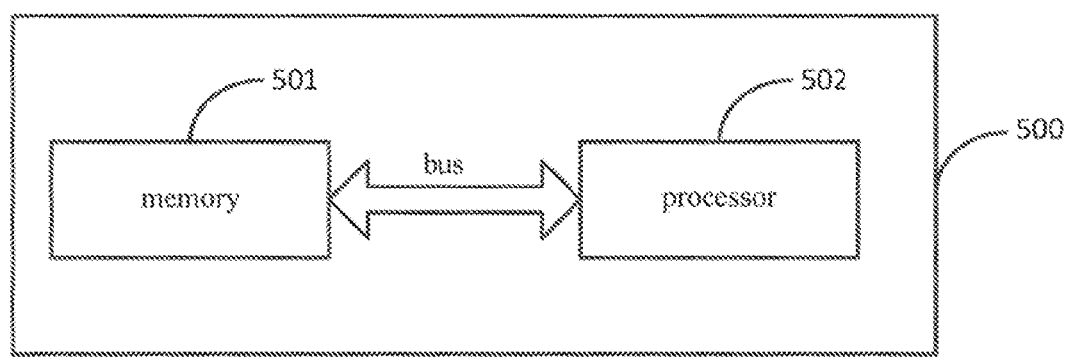
FIG. 5 shows a schematic structural diagram of a computer device 500 provided by an embodiment of the present disclosure.

As shown in FIG. 5, an embodiment of the present disclosure provides a computer device 500 configured to execute the method of detecting circulating abnormal cells in FIG. 1. The computer device 500 comprises a memory 501, a processor 502 and a computer program stored in the memory 501 and executable by the processor 502, wherein the above processor 502 implements the steps of the above method of detecting circulating abnormal cells when executing the above computer program.

Specifically, the above memory 501 and the processor 502 can be a general-purpose memory and processor, which are not specifically defined here. When running the computer program stored in the memory 501, the processor 502 can carry out the above method of detecting circulating abnormal cells.

Corresponding to the method of detecting circulating abnormal cells in FIG. 1, an embodiment of the present disclosure further provides a computer readable storage medium, on which a computer program is stored. The computer program, when executed by the processor, carries out the steps of the above method of detecting circulating abnormal cells.

Specifically, the storage medium can be a general-purpose storage medium, such as a removable magnetic disk and/or a hard disk, and when the computer program in the storage medium is run, the above method of detecting circulating abnormal cells can be carded out.

In the embodiments provided by the present disclosure, it is appreciated that the disclosed system and method can be implemented in other ways. The system embodiments described above are only schematic. For example, the division of the units is only a division of logical functions, and there may be other division methods in actual implementation. For another example, a plurality of units or components may be combined or integrated into another system, or some features may be ignored or not carried out. In addition, the shown or discussed mutual coupling or direct coupling or communication connection may be indirect coupling or communication connection through some communication interfaces, systems or units, and may be electrical, mechanical or in other forms.

The unit described as a separate component may or may not be physically separated, and the components displayed as units may or may not be physical units, that is, they may be located in one place or distributed over a plurality of network units. Some or all of the units can be selected according to the actual needs to achieve the object of the technical solution of the embodiment of the present disclosure.

In addition, the respective functional units in the embodiments provided by the present disclosure may be integrated in one processing unit, or may exist as physically individual units, or two or more units may be integrated in one unit.

If the function is implemented in the form of a software functional unit and is sold or used as an independent product, it can be stored in a computer readable storage medium. Based on this understanding, the technical solution of the present disclosure essentially can be embodied in the form of a software product, or the part of the technical solution of the present disclosure that contributes to the prior art or a part of the technical solution can be embodied in the form of a software product, which is stored in a storage medium and includes a number of instructions to make a computer device (which can be a personal computer, a server, or a network device, etc.) perform all or part of the steps of the methods described in various embodiments of the present disclosure. The aforementioned storage medium may be any kind of medium capable of storing program code, such as U disk, mobile hard disk, Read-Only Memory (ROM), Random Access Memory (RAM), magnetic disk and optical disk.

It should be noted that similar symbols and letters indicate similar items in the following drawings, so once an item is defined in one drawing, it does not need to be further defined and explained in the subsequent drawings. Besides, the terms such as "first", "second" and "third" are only used for differentiating descriptions, and shall not be interpreted as indicating or implying relative importance.

The embodiments described above are only specific implementations of the present disclosure, which are intended to illustrate the technical solution of the present disclosure instead of limiting it. The scope of protection of the present disclosure is not limited to the embodiments described above. Although the present disclosure has been described in detail with reference to the aforementioned embodiments, it is appreciated by those of ordinary skill in the art that anyone skilled in the art can modify the technical solutions described in the aforementioned embodiments or can easily think of variations on the technical solutions, or can make equivalent replacements of some technical features in the technical solutions, within the technical scope disclosed in the present disclosure. These modifications, variations or replacements do not make the essence of the corresponding technical solutions deviate from the spirits and scopes of the technical solutions of the embodiments of the present disclosure, and shall all be covered by the scope of protection of the present disclosure. Therefore, the scope of protection of the present disclosure shall be determined by the scope of protection of the claims.

What is claimed is:

1. A method for detecting circulating abnormal cells, comprising:
    segmenting and labelling cell nuclei included in dark field microscope images of a plurality of probe channels respectively, by using an image processing algorithm and a morphological algorithm;
    inputting the dark field microscope images, in which the cell nuclei are labelled, of the plurality of probe channels into a pre-built circulating abnormal cell detection model to acquire a number of staining signals included in each of the labelled cell nuclei in the dark field microscope image of each of the probe channels; and
    for each of the labelled cell nuclei, determining whether the labelled cell nucleus belongs to a circulating abnormal cell, based on the acquired number of the staining signals included in the labelled cell nucleus in the dark field microscope image of each of the probe channels,
    wherein building the circulating abnormal cell detection model comprises:
        segmenting and labelling the cell nuclei included in the dark field microscope sample images of the plurality of probe channels respectively by using the image processing algorithm and the morphological algorithm, and segmenting the dark field microscope sample images, in which the cell nuclei are labelled, of the probe channels to acquire a plurality of cell nucleus sample images;
        for each of the cell nucleus sample images, performing multiple convolution processes on the cell nucleus sample image to respectively acquire a first feature image, a second feature image, a third feature image, and a fourth feature image;
        performing a convolution process on the fourth feature image to acquire a fifth feature image, and performing upsampling on the fifth feature image to acquire a sixth feature image;
        performing a convolution process on the third feature image and the sixth feature image to acquire a seventh feature image, and performing upsampling on the seventh feature image to acquire an eighth feature image;
        performing a convolution process on the second feature image and the eighth feature image to acquire a ninth feature image, and performing upsampling on the ninth feature image to acquire a tenth feature image;
        performing a convolution process on the first feature image and the tenth feature image to acquire an eleventh feature image; and
        training and testing a deep learning network by taking each of the cell nucleus sample images as an input of the deep learning network, fusing the seventh feature image, the ninth feature image, and the eleventh feature image as output prediction results in three scales of the deep learning network, and finally taking the number of the staining signals included in the labelled cell nuclei in the cell nucleus sample images as the output of the deep learning network, to acquire a circulating abnormal cell detection model, and
    wherein performing the multiple convolution processes on the cell nucleus sample image to respectively acquire the first feature image, the second feature image, the third feature image, and the fourth feature image comprises:
   sequentially performing convolution processes of a first convolution layer, a second convolution layer, a third convolution layer, and a fourth convolution layer on the cell nucleus sample image to acquire the first feature image;
   performing convolution processes of a fifth convolution layer and a sixth convolution layer on the first feature image to acquire the second feature image;
   performing convolution processes of a seventh convolution layer and an eighth convolution layer on the second feature image to acquire the third feature image; and
   performing convolution processes of a ninth convolution layer and a tenth convolution layer on the third feature image to acquire the fourth feature image.

2. The method according to claim 1, wherein in sequentially performing the convolution processes of the first convolution layer, the second convolution layer, the third convolution layer, and the fourth convolution layer on the cell nucleus sample image to acquire the first feature image:
   a size of the cell nucleus sample image is 320*320, a number of convolution kernels of the first convolution layer is 32, a size of the convolution kernels is 3*3 and a step size is 1, and a size of the output feature image is 320*320;
   the second convolution layer comprises a first convolution sublayer and a second convolution sublayer, wherein a number of convolution kernels of the first convolution sublayer is 32, a size of the convolution kernels is 3*3 and a step size is 2, and a size of the output feature image is 160*160;
   and a number of convolution kernels of the second convolution sublayer is 64, a size of the convolution kernels is 1*1 and a step size is 1, and a size of the output feature image is 160*160;
   the third convolution layer comprises a third convolution sublayer and a fourth convolution sublayer, wherein a number of convolution kernels of the third convolution sublayer is 64, a size of the convolution kernels is 3*3 and a step size is 1, and a size of the output feature image is 160*160; and a number of convolution kernels of the fourth convolution sublayer is 128, a size of the convolution kernels is 1*1 and a step size is 2, and a size of the output feature image is 80*80; and
   the fourth convolution layer comprises a fifth convolution sublayer and a sixth convolution sublayer, wherein a number of convolution kernels of the fifth convolution sublayer is 128, a size of the convolution kernel is 3*3 and a step size is 1, and a size of the output feature image is 80*80; and a number of convolution kernels of the sixth convolution sublayer is 128, a size of the convolution kernels is 1*1 and a step size is 1, and a size of the output feature image is 80*80, the feature image output by the sixth convolution sublayer being the first feature image.

3. The method according to claim 1, wherein segmenting and labelling the cell nuclei included in the dark field microscope images of the plurality of probe channels respectively by using the image processing algorithm and the morphological algorithm comprises:
   for the dark field microscope image of each of the probe channels, performing Gaussian kernel filtering on the dark field microscope image to acquire a denoised image;
   labelling connected domains of the denoised image to acquire labelled connected domains; and
   segmenting the acquired connected domains by using the morphological algorithm, and labelling the segmented domains to acquire labelled cell nuclei.

4. The method according to claim 1, wherein inputting the dark field microscope images, in which the cell nuclei are labelled, of the plurality of probe channels into the pre-built circulating abnormal cell detection model to acquire the number of staining signals included in each of the labelled cell nuclei in the dark field microscope image of each of the probe channels comprises:
   inputting a dark field microscope image in which the cell nuclei are labelled of a first probe channel into the circulating abnormal cell detection model to acquire a first count of staining signals included in each of the labelled cell nuclei in the dark field microscope image, in which the cell nuclei are labelled, of the first probe channel;
   inputting a dark field microscope image in which the cell nuclei are labelled of a second probe channel into the circulating abnormal cell detection model to acquire a second count of staining signals included in each of the labelled cell nuclei in the dark field microscope image, in which the cell nuclei are labelled, of the second probe channel;
   inputting a dark field microscope image in which the cell nuclei are labelled of a third probe channel into the circulating abnormal cell detection model to acquire a third count of staining signals included in each of the labelled cell nuclei in the dark field microscope image, in which the cell nuclei are labelled, of the third probe channel; and
   inputting a dark field microscope image in which the cell nuclei are labelled of a fourth probe channel into the circulating abnormal cell detection model to acquire a fourth count of staining signals included in each of the labelled cell nuclei in the dark field microscope image, in which the cell nuclei are labelled, of the fourth probe channel.

5. The method according to claim 4, wherein for each of the labelled cell nuclei, determining whether the labelled cell nucleus belongs to a circulating abnormal cell based on the acquired number of the staining signals included in the labelled cell nucleus in the dark field microscope image of each of the probe channels comprises:
   acquiring a first count of staining signals included in a first labelled cell nucleus in the dark field microscope image, in which the cell nuclei are labelled, of the first probe channel;
   acquiring a second count of staining signals included in the first labelled cell nucleus in a dark field microscope image, in which the cell nuclei are labelled, of a second probe channel;
   acquiring a third count of staining signals included in the first labelled cell nucleus in a dark field microscope image, in which the cell nuclei are labelled, of a third probe channel;
   acquiring a fourth count of staining signals included in the first labelled cell nucleus in a dark field microscope image, in which the cell nuclei are labelled, of a fourth probe channel; and
   determining whether the first labelled cell nucleus belongs to a circulating abnormal cell based on the first count, the second count, the third count, and the fourth count of the staining signals.

6. An electronic device, comprising: a memory, a processor, and a bus, wherein the memory stores machine readable instructions executable by the processor; when the electronic device is operating, the processor communicates with the memory through the bus; and when the machine readable instructions are executed by the processor, following steps of a method for detecting circulating abnormal cells, said steps comprising:

segmenting and labelling cell nuclei included in dark field microscope images of a plurality of probe channels respectively, by using an image processing algorithm and a morphological algorithm;

inputting the dark field microscope images, in which the cell nuclei are labelled, of the plurality of probe channels into a pre-built circulating abnormal cell detection model to acquire a number of staining signals included in each of the labelled cell nuclei in the dark field microscope image of each of the probe channels; and for each of the labelled cell nuclei, determining whether the labelled cell nucleus belongs to a circulating abnormal cell, based on the acquired number of the staining signals included in the labelled cell nucleus in the dark field microscope image of each of the probe channels, wherein building the circulating abnormal cell detection model comprises:

segmenting and labelling the cell nuclei included in the dark field microscope sample images of the plurality of probe channels respectively by using the image processing algorithm and the morphological algorithm, and segmenting the dark field microscope sample images, in which the cell nuclei are labelled, of the probe channels to acquire a plurality of cell nucleus sample images;

for each of the cell nucleus sample images, performing multiple convolution processes on the cell nucleus sample image to respectively acquire a first feature image, a second feature image, a third feature image, and a fourth feature image;

performing a convolution process on the fourth feature image to acquire a fifth feature image, and performing upsampling on the fifth feature image to acquire a sixth feature image;

performing a convolution process on the third feature image and the sixth feature image to acquire a seventh feature image, and performing upsampling on the seventh feature image to acquire an eighth feature image;

performing a convolution process on the second feature image and the eighth feature image to acquire a ninth feature image, and performing upsampling on the ninth feature image to acquire a tenth feature image;

performing a convolution process on the first feature image and the tenth feature image to acquire an eleventh feature image; and training and testing a deep learning network by taking each of the cell nucleus sample images as an input of the deep learning network, fusing the seventh feature image, the ninth feature image, and the eleventh feature image as output prediction results in three scales of the deep learning network, and finally taking the number of the staining signals included in the labelled cell nuclei in the cell nucleus sample images as the output of the deep learning network, to acquire a circulating abnormal cell detection model, and wherein performing the multiple convolution processes on the cell nucleus sample image to respectively acquire the first feature image, the second feature image, the third feature image, and the fourth feature image comprises:

sequentially performing convolution processes of a first convolution layer, a second convolution layer, a third convolution layer, and a fourth convolution layer on the cell nucleus sample image to acquire the first feature image;

performing convolution processes of a fifth convolution layer and a sixth convolution layer on the first feature image to acquire the second feature image;

performing convolution processes of a seventh convolution layer and an eighth convolution layer on the second feature image to acquire the third feature image; and performing convolution processes of a ninth convolution layer and a tenth convolution layer on the third feature image to acquire the fourth feature image.

7. The electronic device according to claim 6, wherein in sequentially performing the convolution processes of the first convolution layer, the second convolution layer, the third convolution layer, and the fourth convolution layer on the cell nucleus sample image to acquire the first feature image:

a size of the cell nucleus sample image is 320*320, a number of convolution kernels of the first convolution layer is 32, a size of the convolution kernels is 3*3 and a step size is 1, and a size of the output feature image is 320*320;

the second convolution layer comprises a first convolution sublayer and a second convolution sublayer, wherein a number of convolution kernels of the first convolution sublayer is 32, a size of the convolution kernels is 3*3 and a step size is 2, and a size of the output feature image is 160*160; and a number of convolution kernels of the second convolution sublayer is 64, a size of the convolution kernels is 1*1 and a step size is 1, and a size of the output feature image is 160*160;

the third convolution layer comprises a third convolution sublayer and a fourth convolution sublayer, wherein a number of convolution kernels of the third convolution sublayer is 64, a size of the convolution kernels is 3*3 and a step size is 1, and a size of the output feature image is 160*160; and a number of convolution kernels of the fourth convolution sublayer is 128, a size of the convolution kernels is 1*1 and a step size is 2, and a size of the output feature image is 80*80; and the fourth convolution layer comprises a fifth convolution sublayer and a sixth convolution sublayer, wherein a number of convolution kernels of the fifth convolution sublayer is 128, a size of the convolution kernel is 3*3 and a step size is 1, and a size of the output feature image is 80*80; and a number of convolution kernels of the sixth convolution sublayer is 128, a size of the convolution kernels is 1*1 and a step size is 1, and a size of the output feature image is 80*80, the feature image output by the sixth convolution sublayer being the first feature image.

8. The electronic device according to claim 6, wherein segmenting and labelling the cell nuclei included in the dark field microscope images of the plurality of probe channels respectively by using the image processing algorithm and the morphological algorithm comprises:

for the dark field microscope image of each of the probe channels, performing Gaussian kernel filtering on the dark field microscope image to acquire a denoised image;

labelling connected domains of the denoised image to acquire labelled connected domains; and segmenting the acquired connected domains by using the morphological algorithm, and labelling the segmented domains to acquire labelled cell nuclei.

9. The electronic device according to claim 6, wherein inputting the dark field microscope images, in which the cell nuclei are labelled, of the plurality of probe channels into the pre-built circulating abnormal cell detection model to acquire the number of staining signals included in each of the labelled cell nuclei in the dark field microscope image of each of the probe channels comprises:

inputting a dark field microscope image in which the cell nuclei are labelled of a first probe channel into the circulating abnormal cell detection model to acquire a first count of staining signals included in each of the labelled cell nuclei in the dark field microscope image, in which the cell nuclei are labelled, of the first probe channel;

inputting a dark field microscope image in which the cell nuclei are labelled of a second probe channel into the circulating abnormal cell detection model to acquire a second count of staining signals included in each of the labelled cell nuclei in the dark field microscope image, in which the cell nuclei are labelled, of the second probe channel;

inputting a dark field microscope image in which the cell nuclei are labelled of a third probe channel into the circulating abnormal cell detection model to acquire a third count of staining signals included in each of the labelled cell nuclei in the dark field microscope image, in which the cell nuclei are labelled, of the third probe channel; and inputting a dark field microscope image in which the cell nuclei are labelled of a fourth probe channel into the circulating abnormal cell detection model to acquire a fourth count of staining signals included in each of the labelled cell nuclei in the dark field microscope image, in which the cell nuclei are labelled, of the fourth probe channel.

10. The electronic device according to claim 9, wherein for each of the labelled cell nuclei, determining whether the labelled cell nucleus belongs to a circulating abnormal cell based on the acquired number of the staining signals included in the labelled cell nucleus in the dark field microscope image of each of the probe channels comprises:

acquiring a first count of staining signals included in a first labelled cell nucleus in the dark field microscope image, in which the cell nuclei are labelled, of the first probe channel;

acquiring a second count of staining signals included in the first labelled cell nucleus in a dark field microscope image, in which the cell nuclei are labelled, of a second probe channel;

acquiring a third count of staining signals included in the first labelled cell nucleus in a dark field microscope image, in which the cell nuclei are labelled, of a third probe channel;

acquiring a fourth count of staining signals included in the first labelled cell nucleus in a dark field microscope image, in which the cell nuclei are labelled, of a fourth probe channel; and determining whether the first labelled cell nucleus belongs to a circulating abnormal cell based on the first count, the second count, the third count, and the fourth count of the staining signals.

11. A non-transitory computer readable storage medium on which a computer program is stored, wherein the computer program, when executed by a processor, performs following steps of a method for detecting circulating abnormal cells:

segmenting and labelling cell nuclei included in dark field microscope images of a plurality of probe channels respectively, by using an image processing algorithm and a morphological algorithm;

inputting the dark field microscope images, in which the cell nuclei are labelled, of the plurality of probe channels into a pre-built circulating abnormal cell detection model to acquire a number of staining signals included in each of the labelled cell nuclei in the dark field microscope image of each of the probe channels; and for each of the labelled cell nuclei, determining whether the labelled cell nucleus belongs to a circulating abnormal cell, based on the acquired number of the staining signals included in the labelled cell nucleus in the dark field microscope image of each of the probe channels, wherein building the circulating abnormal cell detection model comprises:

segmenting and labelling the cell nuclei included in the dark field microscope sample images of the plurality of probe channels respectively by using the image processing algorithm and the morphological algorithm, and segmenting the dark field microscope sample images, in which the cell nuclei are labelled, of the probe channels to acquire a plurality of cell nucleus sample images;

for each of the cell nucleus sample images, performing multiple convolution processes on the cell nucleus sample image to respectively acquire a first feature image, a second feature image, a third feature image, and a fourth feature image;

performing a convolution process on the fourth feature image to acquire a fifth feature image, and performing upsampling on the fifth feature image to acquire a sixth feature image;

performing a convolution process on the third feature image and the sixth feature image to acquire a seventh feature image, and performing upsampling on the seventh feature image to acquire an eighth feature image;

performing a convolution process on the second feature image and the eighth feature image to acquire a ninth feature image, and performing upsampling on the ninth feature image to acquire a tenth feature image;

performing a convolution process on the first feature image and the tenth feature image to acquire an eleventh feature image; and training and testing a deep learning network by taking each of the cell nucleus sample images as an input of the deep learning network, fusing the seventh feature image, the ninth feature image, and the eleventh feature image as output prediction results in three scales of the deep learning network, and finally taking the number of the staining signals included in the labelled cell nuclei in the cell nucleus sample images as the output of the deep learning network, to acquire a circulating abnormal cell detection model, wherein performing the multiple convolution processes on the cell nucleus sample image to respectively acquire the first feature image, the second feature image, the third feature image, and the fourth feature image comprises:

sequentially performing convolution processes of a first convolution layer, a second convolution layer, a third convolution layer, and a fourth convolution layer on the cell nucleus sample image to acquire the first feature image;

performing convolution processes of a fifth convolution layer and a sixth convolution layer on the first feature image to acquire the second feature image;

performing convolution processes of a seventh convolution layer and an eighth convolution layer on the second feature image to acquire the third feature image; and performing convolution processes of a ninth convolution layer and a tenth convolution layer on the third feature image to acquire the fourth feature image.

\* \* \* \* \*